United States Patent [19]
Hwang

[11] Patent Number: 5,398,812
[45] Date of Patent: Mar. 21, 1995

[54] FINGERPRINT SYSTEMS EMPLOYING IODINE-BASED MARKING FLUID

[76] Inventor: Michael Y. S. Hwang, 11001 Rutledge Dr., Gaithersburg, Md. 20878

[21] Appl. No.: 187,201

[22] Filed: Jan. 27, 1994

[51] Int. Cl.6 .............................................. B65D 69/00
[52] U.S. Cl. .................................. 206/568; 206/225; 118/31.5; 106/20 R; 427/1
[58] Field of Search ............... 206/223, 568, 569, 229, 206/81, 524.1, 524.3, 225; 118/31.5; 106/19 R, 20 R; 427/1

[56] References Cited
U.S. PATENT DOCUMENTS

| | | | |
|---|---|---|---|
| 4,190,056 | 2/1980 | Tappes et al. | 427/1 X |
| 4,294,349 | 10/1981 | Ibsen et al. | 206/568 X |
| 5,143,210 | 9/1992 | Warwick et al. | 206/569 X |

Primary Examiner—Jacob K. Ackun, Jr.

[57] ABSTRACT

A marking system comprising a rigid container and a quantity of fabric located therein and a quantity of marking fluid to saturate the fabric, the marking fluid comprised of a two to nine percent iodine in ethanol solution and the iodine/ethanol solution being mixed with about the same amount of water.

1 Claim, 3 Drawing Sheets

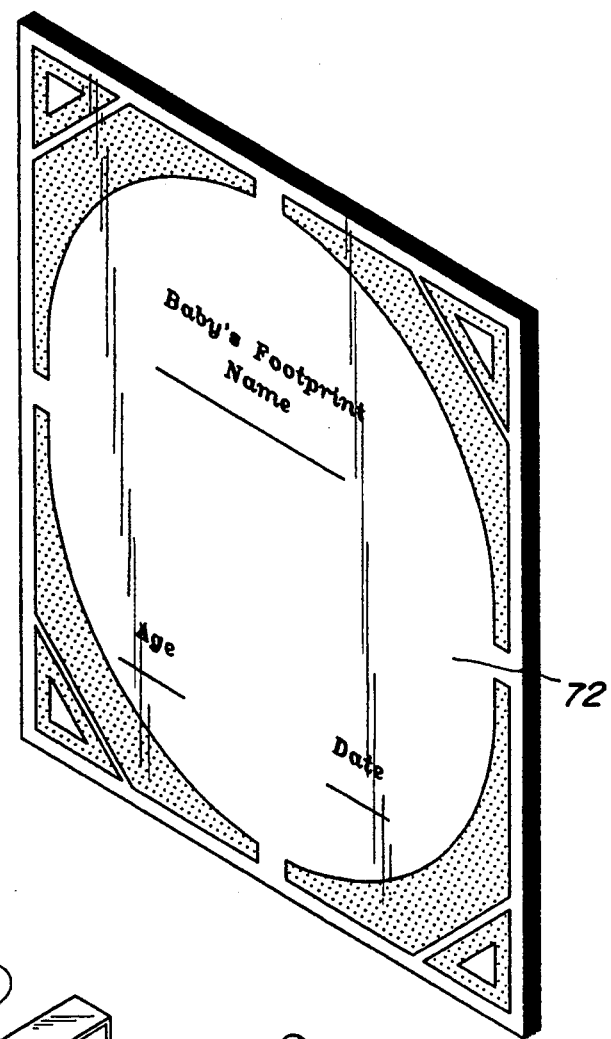
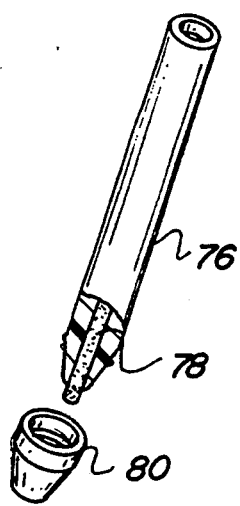
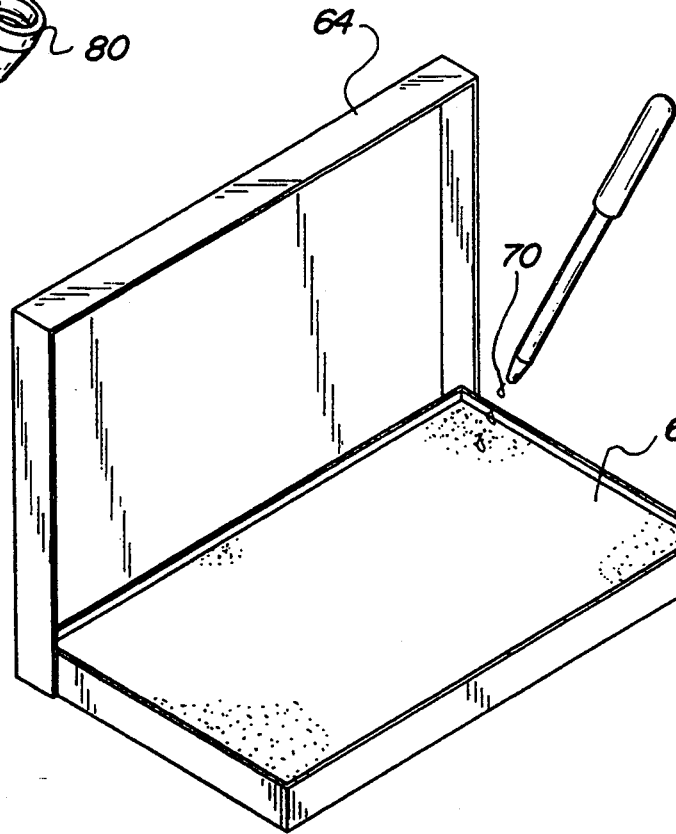
Fig. 5
Fig. 7
Fig. 6

FINGERPRINT SYSTEMS EMPLOYING IODINE-BASED MARKING FLUID

BACKGROUND OF THE INVENTION

1. Field of the Invention

The present invention relates to fingerprint systems employing iodine-based marking fluid and more particularly pertains to employing an iodine-based fluid for fingerprinting and other marking functions.

2. Description of the Prior Art

The use of fingerprinting systems is known in the prior art. More specifically, fingerprinting systems heretofore devised and utilized for the purpose of marking with oil-based fluids are known to consist basically of familiar, expected, and obvious structural configurations, notwithstanding the myriad of designs encompassed by the crowded prior art which has been developed for the fulfillment of countless objectives and requirements.

The prior art discloses a large number of fingerprinting systems. By way of example, U.S. Pat. No. 3,549,397 to McDonald discloses a method for developing finger prints.

U.S. Pat. No. 4,029,012 to Smith,III discloses a two-part inkless applicator for fingerprints.

U.S. Pat. No. 4,258,073 to Payne discloses methods for the taking of finger prints.

U.S. Pat. No. 4,262,623 to Smith,III discloses an inkless fingerprinting device and method adapted for recordation of a plurality of fingerprints.

U.S. Pat. No. 4,363,286 to Leavitt discloses a fingerprinting packet.

U.S. Pat. No. 5,009,919 to Vassiliades discloses a fingerprinting system and method.

In this respect, fingerprint systems employing iodine-based marking fluid according to the present invention substantially depart from the conventional concepts and designs of the prior art, and in doing so provide an apparatus primarily developed for the purpose of employing an iodine-based fluid for fingerprinting and other marking functions.

Therefore, it can be appreciated that there exists a continuing need for new and improved fingerprint systems employing iodine-based marking fluid which can be used for employing an iodine-based fluid for fingerprinting and other marking functions. In this regard, the present invention substantially fulfills this need.

SUMMARY OF THE INVENTION

In view of the foregoing disadvantages inherent in the known types of fingerprinting systems now present in the prior art, the present invention provides improved fingerprint systems employing iodine-based marking fluid. As such, the general purpose of the present invention, which will be described subsequently in greater detail, is to provide new and improved fingerprint systems employing iodine-based marking fluid and methods which have all the advantages of the prior art and none of the disadvantages.

To attain this, the present invention essentially comprises a new and improved fingerprint kit employing iodine-based marking fluid comprising, in combination, a box having rectangular side walls coupled together with an upper lid, a lower lid, and an intermediate support surface dividing the box into an upper compartment and a lower compartment; the lower compartment including the lower lid pivotable with respect thereto for the storage of documents for being marked; the upper compartment containing marking material including a stamp pad with an absorbent fabric material for receiving the marking fluid, a bottle containing the marking fluid, an eyedropper for dispensing the marking fluid from the bottle to the pad and a dispenser with a roll of fingerprint paper for receiving fingerprint impressions from the pad; the fingerprint dispenser including a slide plate with a housing at one end for receiving a roll of paper and a slot with a knife at the interface between the plate and the housing for the sequential dispensing of fingerprint paper for receiving the fingerprints; and the fingerprint fluid being comprised of a two to nine percent solution of iodine in ethanol diluted with about the same amount of water, the final solution being reddish brown, light brown on the skin but dark blue on the paper when mixed with starch normally present on the surfaces of paper.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent of legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide new and improved fingerprint systems employing iodine-based marking fluid which have all the advantages of the prior art fingerprinting systems and none of the disadvantages.

It is another object of the present invention to provide new and improved fingerprint systems employing iodine-based marking fluid which may be easily and efficiently manufactured and marketed.

It is a further object of the present invention to provide new and improved fingerprint systems employing iodine-based marking fluid which are of a durable and reliable construction.

An even further object of the present invention is to provide new and improved fingerprint systems employing iodine-based marking fluid which are susceptible of a low cost of manufacture with regard to both materials and labor, and which accordingly are then susceptible of low prices of sale to the consuming public, thereby making such fingerprint systems employing iodine-based marking fluid economically available to the buying public.

Still yet another object of the present invention is to provide new and improved fingerprint systems employing iodine-based marking fluid which provide in the apparatuses and methods of the prior art some of the advantages thereof, while simultaneously overcoming some of the disadvantages normally associated therewith.

Even still another object of the present invention is to employ an iodine-based fluid for fingerprinting and other marking functions.

Lastly, it is an object of the present invention to provide a marking system comprising a rigid container and a quantity of fabric located therein and a quantity of marking fluid to saturate the fabric, the marking fluid comprised of a two to nine percent iodine in ethanol solution and the iodine/ethanol solution being mixed with about the same amount of water.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 5 is a perspective view of a recipient surface for receiving the footprint of a baby and other information illustrating an alternate embodiment of the invention.

FIG. 6 is a perspective illustration of the stamp pad and eyedropper similar to that shown in FIG. 1 but sized for use with the alternate embodiment of the invention.

FIG. 7 is a perspective view of a marking pen constituting another alternate embodiment of the invention with parts broken away to show certain internal constructions thereof.

The same reference numerals refer to the same parts throughout the various figures.

DESCRIPTION OF THE PREFERRED EMBODIMENT

Figure 1:
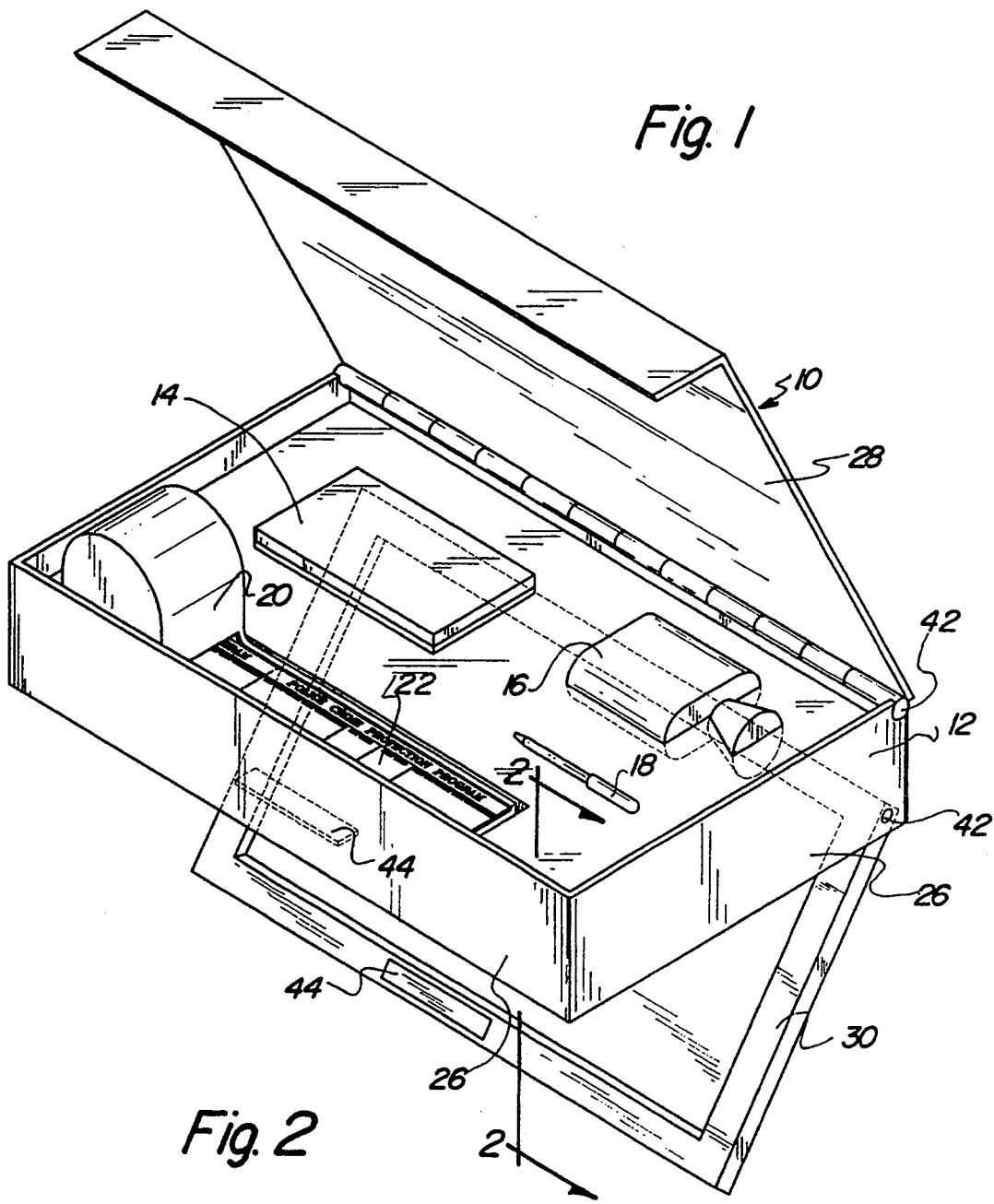
FIG. 1 is a perspective illustration of the preferred embodiment of the fingerprint system employing iodine-based marking fluid constructed in accordance with the principles of the present invention.
Figure 2:
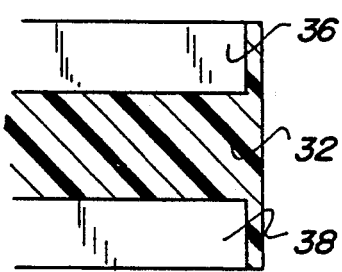
FIG. 2 is a cross-sectional view taken along line 2—2 of FIG. 1.
Figure 3:
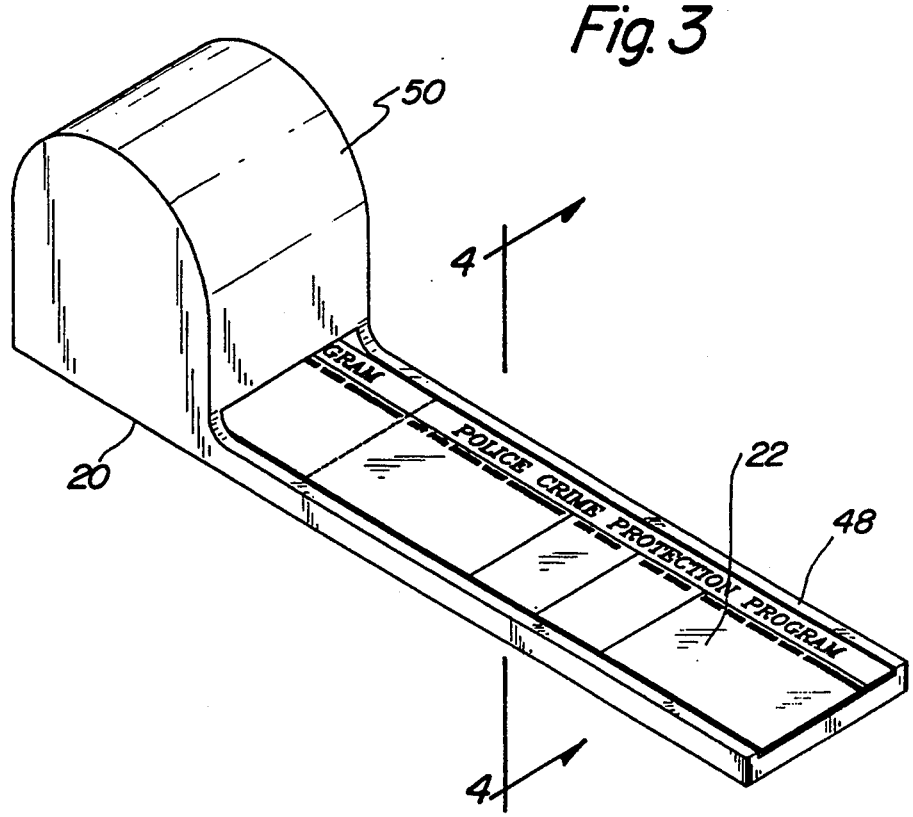
FIG. 3 is a perspective illustration of the row of paper for fingerprinting.
Figure 4:
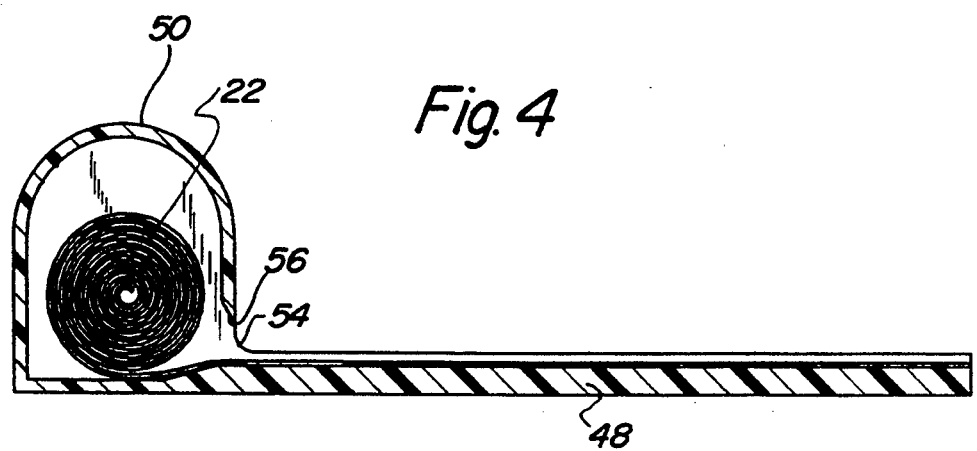
FIG. 4 is a sectional view taken along line 4—4 of FIG. 3.

With reference now to the drawings, and in particular to FIGS. 1 through 4 thereof, the preferred embodiment of the new and improved fingerprint systems employing iodine-based marking fluid embodying the principles and concepts of the present invention and generally designated by the reference numeral 10 will be described.

Specifically, it will be noted in FIGS. 1 through 4 that there is provided a fingerprint system 10. In its broadest context, the system 10 includes a box 12, a stamp pad 14, a bottle of marking fluid 16, an eyedropper 18, and a dispenser for paper 22 to receive the fingerprints. These components function together for their intended objectives and purposes.

More specifically, the box 12 is rectangular in configuration. It is formed with rectangular side walls, front wall and rear wall 26. The various walls are coupled together in a rectangular configuration and include an upper lid 28 and a lower lid 30. An intermediate support surface 32, parallel with the upper and lower lids when closed, separate the box into an upper component 36 and a lower component 38. These components may be opened and closed individually for providing access to the contents therein. Hinges 42 couple the lids to the side walls 26. Magnets 44 on the lids insure that the lids are retained closed when so intended.

The lower compartment 38 is of a generally rectangular configuration. It is intended to receive sheet material, preferably paper, of the type to be marked with the ink contained within the bottle 16. Dispensing is by using the eyedropper 18 onto a fabric, preferably nonwoven, located in the stamp pad 14 in the conventional manner. Such material to be marked may include, for example, baby certificates for receiving footprints or the like. Such lower compartment may also be used to store such certificates after being marked in the intended manner.

The upper compartment is for receiving a plurality of objects. It is preferred that the lower surface of the upper compartment be contoured for receiving such components. Note FIG. 1. Such components located in the upper compartment include the stamp pad 14, the bottle 16 for the ink or marking fluid, an eyedropper 18 for dispensing fluid from the bottle to the stamp pad and a container 20 for sheet material, preferably paper 22 for receiving fingerprints.

The fingerprint dispenser 20 is provided with a slide plate 48 and a housing 50 at one end of the slide plate. The housing is for receiving the roll of paper 22. Such paper is initially in roll form. Note FIG. 4. At the interface between the slide plate 48 and the dispenser 50 is a slot 54 for the movement of the paper therethrough from its storage orientation within the housing to a planar orientation on the slide plate whereat fingerprints are marked on the paper. Located above the slot is a knife 56 for separating the paper after receiving fingerprints. Subsequent paper may be pulled from the roll thereafter for additional fingerprinting.

Located within the bottle 16 is the fingerprint fluid. The fingerprint fluid is comprised of two to nine percent solution of iodine in ethanol. Such solution is diluted with about the same amount of water. The final solution for use is reddish-brown or light brown in color when on the skin or in the bottle. Such color of the fluid changes to dark blue on the paper when the paper is of the type mixed with starch which is normally present on the surfaces of paper. Although a six to nine percent solution has been found adequate for the intended purposes, the preferred quantity of iodine in the iodine/ethanol solution is about six percent of iodine.

Shown in FIGS. 5 and 6 is an alternate embodiment of the invention. In such embodiment, the stamp pad 60 is of an enlarged configuration. It includes a base 62 and a lid 64 adapted to seal the contents therebetween. Such contents is a pad 68 of a fabric material, preferably of a matted or felted material adapted to receive and retain a quantity of marking fluid therein. The construction of the stamp pad 60 is essentially the same as that of the stamp pad 14 of FIG. 1 except for its enlarged size. Also shown in FIG. 6 is the eyedropper dispensing the marking liquid 70 onto the pad for use. In this embodiment, it is intended that the footprint of a baby being marked with marking fluid and the impression thereof provided on a sheet 72 of paper as a permanent record of the baby for identification and sentimental purposes. The recipient surface 72 for the footprint may be of an ornate configuration with the designs in the corner. The sheet is also preferably preprinted with information relating to the baby such as the baby's name, age and date done. A plurality of such sheets 70 may be stored within a box such as box 12 as shown in FIG. 1.

The final embodiment of the invention is illustrated in FIG. 7. In such embodiment, the container for the fabric material to receive the marking fluid 70 is in the form of a rigid tubular shell 76. The shell 76 has therein the fabric material 78 similar to that of the primary embodiment. The cylindrical shape of the shell 76 is that of a marking pen. The marking pen may be used in the conventional way and is preferably provided with a cap 80 for sealing the exposed tip of the fabric containing the marking fluid.

Fingerprinting is a permanent record for individual identification. Conventional fingerprinting is done by pressing fingers into a sticky oil-based dye and imposing them onto a card. This method is messy and inconvenient for most users. The present invention is an individually packed and sealed absorbent paper or unwoven cloth which has been soaked with a special ink formula. When making fingerprints, all one needs to do is open the pack and press fingers on the pad with ink and impose them on the card. There is no need to keep the ink pad or designate a special room for fingerprinting as in most police stations. The ink of the present invention does not stain most surfaces. It is light brown and involves very little cleanup after making the print.

The systems can be sold to law enforcement agencies as well as to gift shops or hospitals as a package for newborn baby finger/foot prints. The package, which will include the system, will furnish an album with nicely pre-printed cards with spaces for baby's name, age and date done. Each card provides a record for a time point of baby's age. Parents will continue to have the baby's fingerprints done in the home after the initial fingerprint at the hospital. The systems can also be sold as toys in shops as magic print because the color will change from brown to dark blue on the paper. The invention is also applicable to marking pens.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new and improved fingerprint kit employing iodine-based marking fluid comprising, in combination:
   a box having rectangular side walls coupled together with an upper lid, a lower lid, and an intermediate support surface dividing the box into an upper compartment and a lower compartment;
   the lower compartment including the lower lid pivotable with respect thereto for the storage of documents for being marked;
   the upper compartment containing marking material including a stamp pad with an absorbent fabric material for receiving the marking fluid, a bottle containing the marking fluid, an eyedropper for dispensing the marking fluid from the bottle to the pad and a dispenser with a roll of fingerprint paper for receiving fingerprint impressions from the pad;
   the fingerprint dispenser including a slide plate with a housing at one end for receiving a roll of paper and a slot with a knife at the interface between the plate and the housing for the sequential dispensing of fingerprint paper for receiving the fingerprints; and
   the fingerprint fluid being comprised of a two to nine percent solution of iodine in ethanol diluted with about the same amount of water, the final solution being reddish brown, light brown on the skin but dark blue on the paper when mixed with starch normally present on the surfaces of paper.

* * * * *